US008083792B2

(12) United States Patent
Boucher et al.

(10) Patent No.: US 8,083,792 B2
(45) Date of Patent: Dec. 27, 2011

(54) PERCUTANEOUS ENDOPROSTHESIS USING SUPRARENAL FIXATION AND BARBED ANCHORS

(75) Inventors: Donald D. Boucher, Boynton Beach, FL (US); Michael Dugery, Doylestown, PA (US); Kirk L. Johnson, Davie, FL (US); Isaac John Khan, Bridgewater, NJ (US); David C. Majercak, Stewartsville, NJ (US); Scott Lyle Rush, Coral Springs, FL (US)

(73) Assignee: Cordis Corporation, Bridgewater, NJ (US)

( * ) Notice: Subject to any disclaimer, the term of this patent is extended or adjusted under 35 U.S.C. 154(b) by 501 days.

(21) Appl. No.: 11/338,281

(22) Filed: Jan. 24, 2006

(65) Prior Publication Data

US 2007/0173929 A1 Jul. 26, 2007

(51) Int. Cl.
*A61F 2/06* (2006.01)
(52) U.S. Cl. ............... 623/1.35; 623/1.11; 623/1.16
(58) Field of Classification Search ............ 623/1.13, 623/1.15–1.16, 1.35–1.36, 1.1, 1.11, 1.2, 623/1.3
See application file for complete search history.

(56) References Cited

U.S. PATENT DOCUMENTS

| 5,397,355 | A | * | 3/1995 | Marin et al. | 623/1.2 |
|---|---|---|---|---|---|
| 5,575,817 | A | * | 11/1996 | Martin | 623/1.35 |
| 5,591,197 | A | * | 1/1997 | Orth et al. | 623/1.16 |
| 5,824,037 | A | * | 10/1998 | Fogarty et al. | 623/1.13 |
| 5,824,042 | A | * | 10/1998 | Lombardi et al. | 623/1.13 |
| 5,843,158 | A |   | 12/1998 | Lenker et al. |   |
| 5,843,167 | A | * | 12/1998 | Dwyer et al. | 623/1.14 |
| 5,868,783 | A | * | 2/1999 | Tower | 606/198 |
| 5,876,418 | A | * | 3/1999 | KarlheinzHauenstein et al. | 606/198 |
| 5,984,955 | A | * | 11/1999 | Wisselink | 623/1.35 |
| 5,993,481 | A | * | 11/1999 | Marcade et al. | 623/1.35 |
| 6,051,020 | A | * | 4/2000 | Goicoechea et al. | 623/1.35 |
| 6,110,198 | A | * | 8/2000 | Fogarty et al. | 623/1.12 |
| 6,162,246 | A | * | 12/2000 | Barone | 623/1.35 |
| 6,187,036 | B1 | * | 2/2001 | Shaolian et al. | 623/1.15 |
| 6,355,056 | B1 | * | 3/2002 | Pinheiro | 623/1.13 |
| 6,517,573 | B1 | * | 2/2003 | Pollock et al. | 623/1.15 |
| 6,648,913 | B1 | * | 11/2003 | Yee et al. | 623/1.35 |
| 6,652,580 | B1 | * | 11/2003 | Chuter et al. | 623/1.36 |

(Continued)

FOREIGN PATENT DOCUMENTS

EP 1621159 A1 2/2006

(Continued)

OTHER PUBLICATIONS

European Search Report dated Jun. 3, 2007 for Application No. 07250232.1.

*Primary Examiner* — Corrine M McDermott
*Assistant Examiner* — Mark Mashack

(57) ABSTRACT

An endoprosthetic device for treating abdominal aortic aneurysms using suprarenal fixation. A stent ring is anchored in an area above the renal arteries using self-flaring barbs that project during the nitinol expansion process. Sutures extend from the stent ring to an area below the renal arteries to a bifurcated trunk portion comprising a nitinol fabric on a non-kinking frame. The bifurcated trunk is sealed proximal the iliac arteries and includes iliac leg holders having self-flaring retention struts for non-traumatic holding of iliac leg prosthetics. Suprarenal fixation and collapsible cells having retention projections and barbs that only flare during the nitinol expansion process assist in lowering the devices profile and sheathability for percutaneous delivery and may provide for recapturing the anchored device.

1 Claim, 6 Drawing Sheets

U.S. PATENT DOCUMENTS

| | | | |
|---|---|---|---|
| 6,663,667 B2* | 12/2003 | Dehdashtian et al. | 623/1.51 |
| 6,733,523 B2* | 5/2004 | Shaolian et al. | 623/1.35 |
| 6,908,477 B2* | 6/2005 | McGuckin et al. | 623/1.11 |
| 6,942,691 B1* | 9/2005 | Chuter | 623/1.35 |
| 7,029,494 B2* | 4/2006 | Soun et al. | 623/1.15 |
| 7,331,992 B2* | 2/2008 | Randall et al. | 623/1.36 |
| 2002/0052643 A1* | 5/2002 | Wholey et al. | 623/1.13 |
| 2002/0193873 A1* | 12/2002 | Brucker et al. | 623/1.35 |
| 2003/0023299 A1* | 1/2003 | Amplatz et al. | 623/1.13 |
| 2003/0130720 A1 | 7/2003 | Depalma et al. | |
| 2003/0176911 A1* | 9/2003 | Iancea et al. | 623/1.13 |
| 2003/0176912 A1* | 9/2003 | Chuter et al. | 623/1.13 |
| 2004/0098098 A1* | 5/2004 | McGuckin et al. | 623/1.14 |
| 2004/0122510 A1* | 6/2004 | Sarac | 623/1.36 |
| 2005/0203607 A1 | 9/2005 | Scherrible | |
| 2005/0228484 A1* | 10/2005 | Stephens et al. | 623/1.16 |
| 2005/0273155 A1 | 12/2005 | Bahler et al. | |
| 2007/0179592 A1* | 8/2007 | Schaeffer | 623/1.35 |

FOREIGN PATENT DOCUMENTS

| | | |
|---|---|---|
| WO | WO 92/06734 A | 4/1992 |
| WO | WO 92/008734 A1 | 4/1992 |
| WO | WO 2004/008996 A1 | 1/2004 |

\* cited by examiner

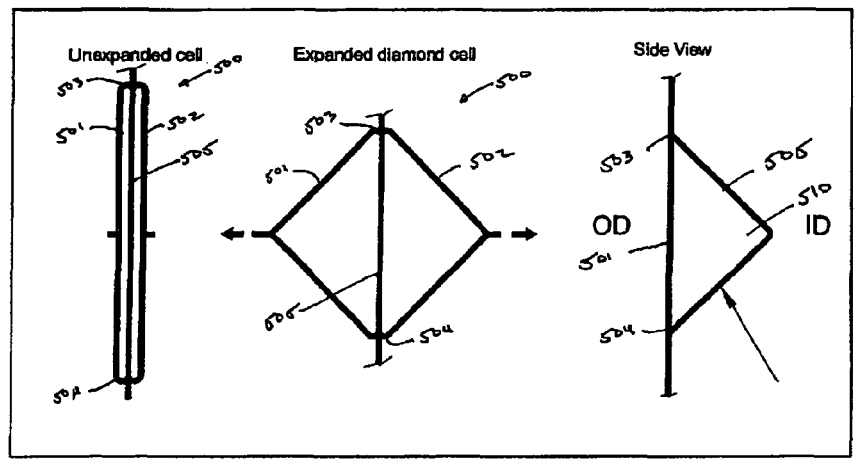
Figure 5
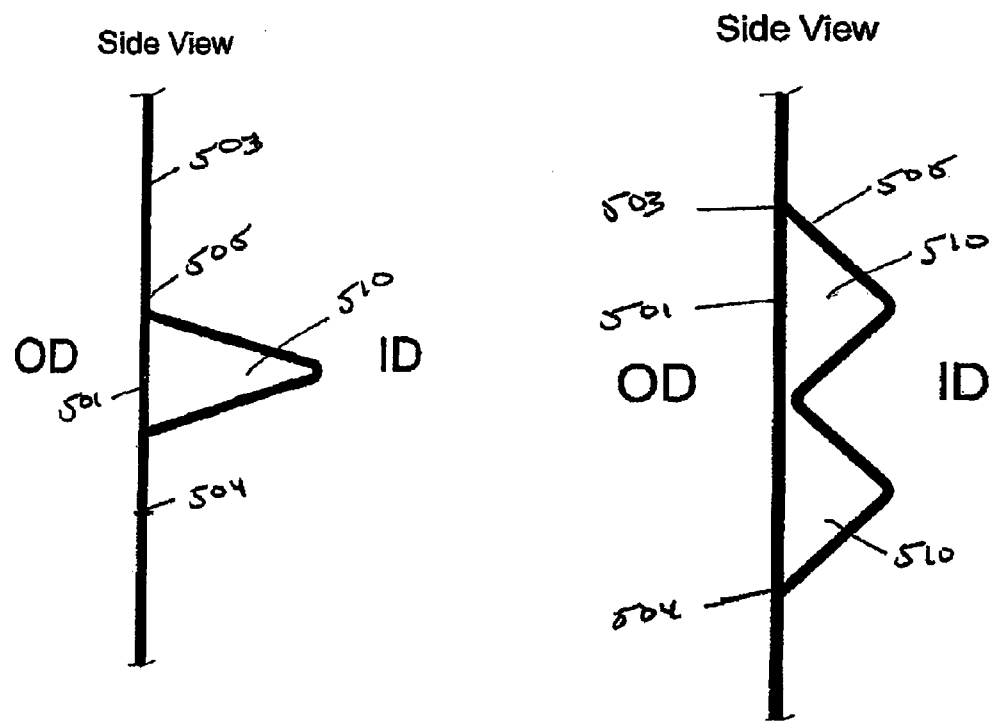
Figure 6A
Figure 6B

PERCUTANEOUS ENDOPROSTHESIS USING SUPRARENAL FIXATION AND BARBED ANCHORS

I. FIELD OF THE INVENTION

The present invention relates to percutaneous prosthetic devices and methods. More particularly, the present invention relates to percutaneous aortic prosthetic devices for treating abdominal aortic aneurysms having improved fixation means and methods

II. BACKGROUND OF THE INVENTION

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located at or below the renal arteries, and may be continuous with iliac aneurysms in one or both of the two iliac arteries. An abdominal aortic aneurysm is often "infrarenal", meaning that there is a portion of healthy abdominal aorta between the aneurysm and the renal arteries. When left untreated, the aneurysm may rupture, usually causing rapid fatal hemorrhaging.

There has been a great deal of research directed at developing less invasive, percutaneous, e.g., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. The delivery procedure typically involves advanced angiographic techniques performed through vascular accesses gained via surgical cutdown of a remote artery, such as the common femoral or brachial arteries. Over a guidewire, the appropriate size introducer will be placed. The catheter and guidewire is passed through the aneurysm, and, with the appropriate size introducer housing a stent-graft, the stent-graft will be advanced along the guidewire to the appropriate position. Typical deployment of the stent-graft device requires withdrawal of an outer sheath while maintaining the position of the stent-graft with an inner-stabilizing device. Many stent-grafts are self-expanding; however, an additional angioplasty procedure, e.g., balloon angioplasty, may be required to secure the position of the stent-graft. Following the placement of the stent-graft, standard angiographic views may be obtained.

While the above-described endoprostheses represent a significant improvement over conventional surgical techniques, there is a need to improve the endoprostheses, their method of use, and their percutaneous delivery. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long term fluid tight seals and anchoring positions. Also, in addressing these difficulties, it must be remembered that these devices must also be configured so as to allow the profile of the device to be collapsed to sizes that are optimal with percutaneous delivery systems.

III. SUMMARY OF THE INVENTION

Various embodiments of the present invention offer advantageous features that may overcome the drawbacks discussed above and offer new advantages as well.

An object of the invention is to provide an endoprosthesis device for delivery with percutaneous systems. A related object of the invention is to provide an endoprosthesis device configured to allow the profile of the device to be reduced to sizes that make it advantageously compatible with percutaneous delivery systems. Another object of the invention is the provision of an endoprosthesis device for treating an abdominal aortic aneurysm.

According to these objects of at least one embodiment of the invention, one aspect of the invention is the provision of an endoprosthesis device having its aortic proximal neck sealing separate from the device's intra-luminal fixation. According to this aspect of at least one embodiment of the invention, one advantageous feature of the invention is the provision of an endoprosthesis device adapted for suprarenal fixation. According to this aspect of at least one embodiment of the invention, a suprarenal stent may provided for device fixation. In a preferred embodiment, the suprarenal stent is attached to a bifurcated body portion via hanging sutures that span the renal arteries. In one embodiment, the bifurcated body portion comprises a nitinol fabric that is welded to a thin frame. Preferably, the nitinol fabric has dimensions of a few microns or less and the frame is a thin nitinol stent that prevents kinking of the assembly, and when deployed, allows the self-expansion of the trunk to seal the proximal aortic neck. In an alternate embodiment, the bifurcated body portion comprises a polymeric material and includes a proximal neck stent placed in-situ for sealing of the graft to the proximal neck. Preferably, the stent includes an anchoring mechanisms, such as hooks or barbs, for attachment and anchoring.

According to these embodiments of the invention, the body portion is also preferably configured to receive iliac leg prostheses allowing for the assembly of the device into a completed endoprosthesis for treating an abdominal aortic aneurysm.

It is another object of the invention to provide anchoring mechanisms and retention mechanisms for use with the endoprosthesis devices and methods of the present invention. It is another object of the invention to provide anchoring and retention mechanisms that may reduce problems encountered with sheathing the associated device. It is yet another object of the invention to provide an anchoring mechanism that may allow for recapturability. According to these objects of the invention, there is provided methods of harnessing the phenomena of diamond foreshortening to construct collapsible cells that include central struts that may be configured to flare out-of-plane in the form of self-flaring barbs or retention projections.

It is a further object of the invention to provide self-flaring mechanisms that may serve as an endoleg retention mechanism that provides non-traumatic holding. It is also an object of the invention to provide self-flaring mechanisms that may act as hooks or barbs for anchoring intra-luminal devices.

According to various objects and advantages of the invention, there is provided a retaining mechanism comprising self-flaring retention projections. According to one aspect of the invention, the retaining mechanisms may comprise nitinol, or other shape-memory alloy, that operationally deploys protrusions during the nitinol expansion process. An advantageous feature of the invention is that the protrusion may be configured to flare out-of-plane during device expansion or deployment to provide interiorly deployed projections mateable with gaps, windows, meshes or the like of other devices.

Also according to the invention, there is provided an intra-luminal device having self-flaring barbs to aid attachment or anchoring of the devices. An advantageous feature of the invention is that the barbs may be configured to flare during device expansion to anchor expanding devices. Anchors configured in this manner may improve sheathabillity and afford a means of recapture. Preferably, the anchoring mechanisms are configured so that only the barbs extend beyond the outer diameter of the device being anchored. One advantageous feature of the invention is that the anchoring mechanisms and retention protrusions may be used on the same device.

In a preferred embodiment, the retention protrusions and self-flaring barbs are the result of the provision of a central strut on a collapsible frame that expands in a manner that forces the strut to bend out of plane. An advantageous feature of the invention is the ability to configure the frame and strut cell assembly to result in an expanded structure having a desired geometry. The cell assembly preferably comprises nitinol or other shape memory alloy that expands after deployment. The cells of the present invention may be included in stents, grafts, endografts or any other intra-luminal device. Moreover, the cells may be part of a composite, mesh, framework or other collapsible structure commonly deployed via catheterization procedures.

Given the following enabling description of the drawings, the advantageous aspects and features of the inventions should become evident to a person of ordinary skill in the art.

IV. BRIEF DESCRIPTION OF THE DRAWINGS

The present invention is described with reference to the accompanying drawings. In the drawings, like reference numerals indicate identical or functionally similar elements.

FIG. 5 illustrates a collapsed and expanded diamond shaped cell having a center strut that is displace out of plane due to foreshortening.

FIG. 6A-B are side views of retention mechanisms for endoleg retention according to the invention.

Figure 7:
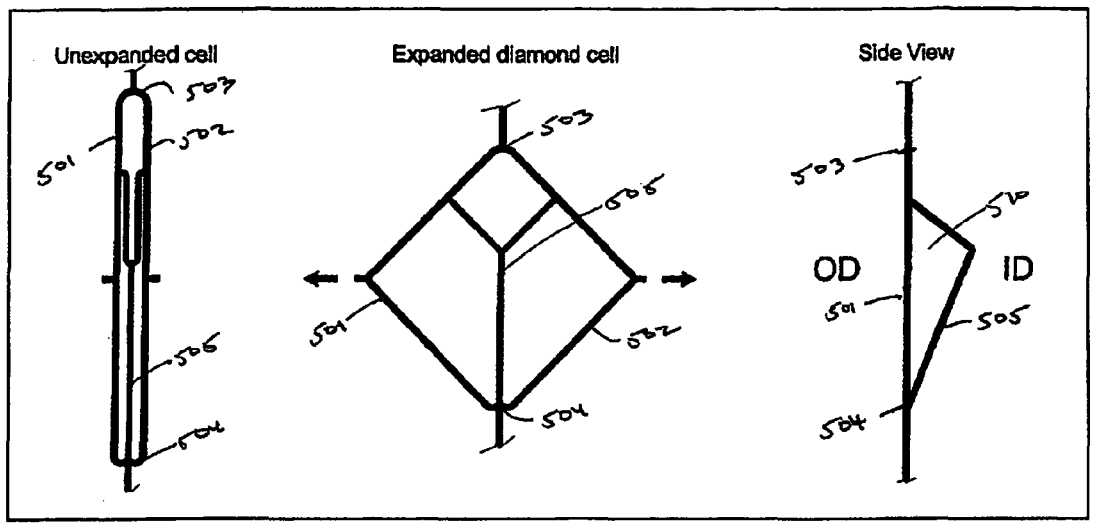

FIG. 7 includes an unexpanded, expanded front view and expanded side view of an embodiment of a cell having a "Y" shaped center strut.

Figure 8:
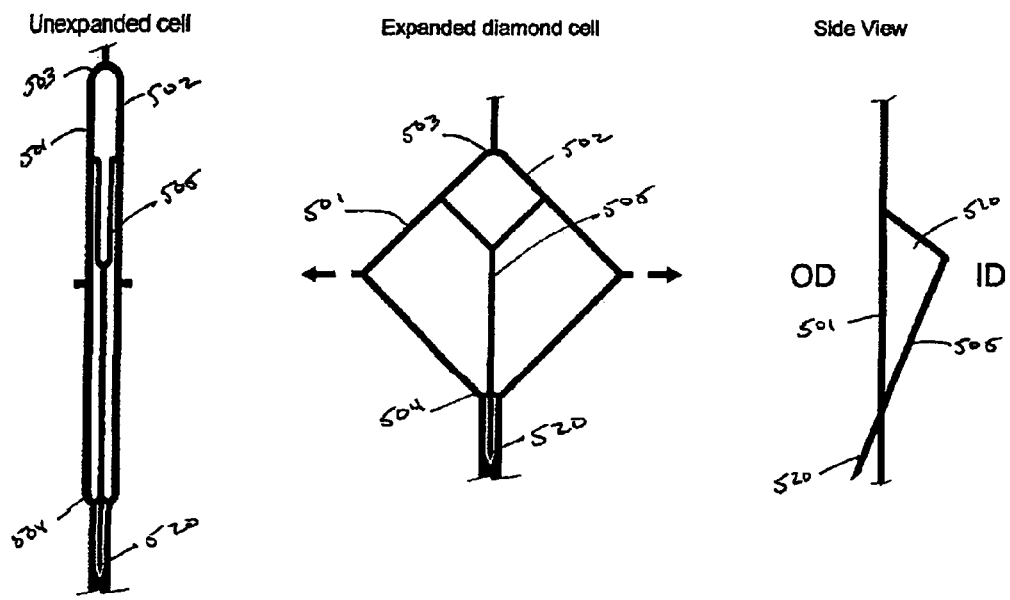

FIG. 8 includes an unexpanded, expanded front view and expanded side view of the cell of FIG. 7 including a self-flaring barb member according to the invention.

Figure 9:
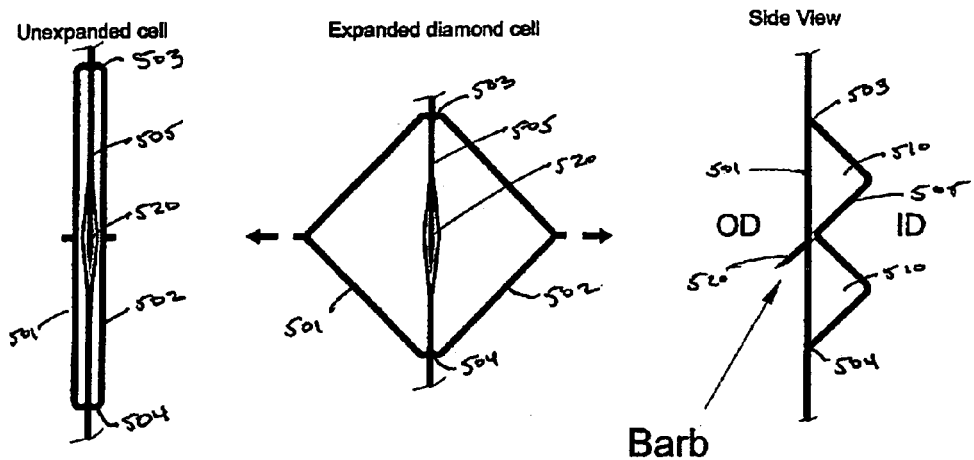

FIG. 9 includes an unexpanded, expanded front view and expanded side view of an alternative embodiment of an anchoring mechanism including a self-flaring barb member according to the invention.

Figure 10:
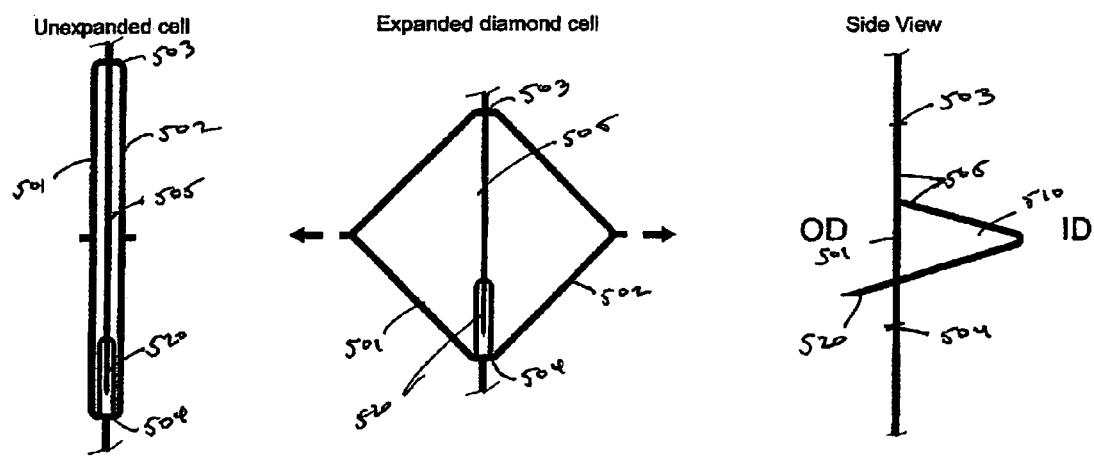

FIG. 10 includes an unexpanded, expanded front view and expanded side view of another alternative embodiment of an anchoring mechanism including a self-flaring barb member according to the invention.

Figure 11:
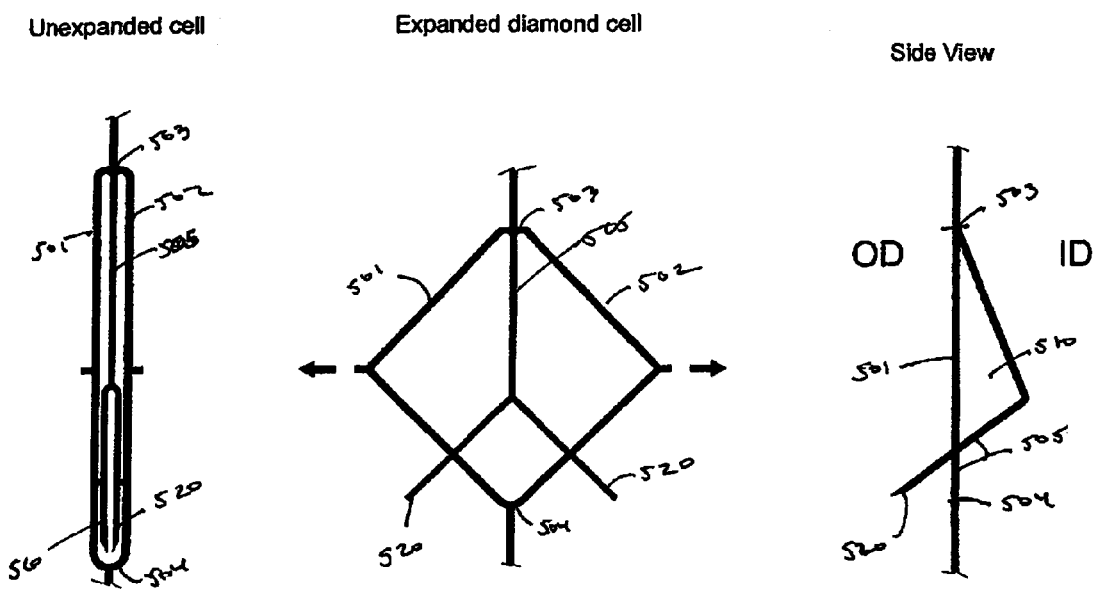

FIG. 11 includes an unexpanded, expanded front view and expanded side view of yet another alternative embodiment of an anchoring mechanism including a self-flaring barb member according to the invention.

V. DETAILED DESCRIPTION OF THE DRAWINGS

The present invention is based, in part, on the discovery that suprarenal fixation of endoprostheses may provide advantageous benefits. The present invention is also based, in part, or the discovery that the phenomena of diamond foreshortening may be harnessed to construct collapsible cells with central struts that may be configured to deploy self-flaring projections, such as barbs or retention mechanisms, for use with intra-luminal devices. While the present invention will be described in connection with an endoprosthesis device for treating an abdominal aortic aneurysm, one of ordinary skill in the art will recognize the universality of the advantageous aspects of the invention, including the applicability in the deployment, repositioning and capture of devices in any intra-luminal procedure.

Figure 1:
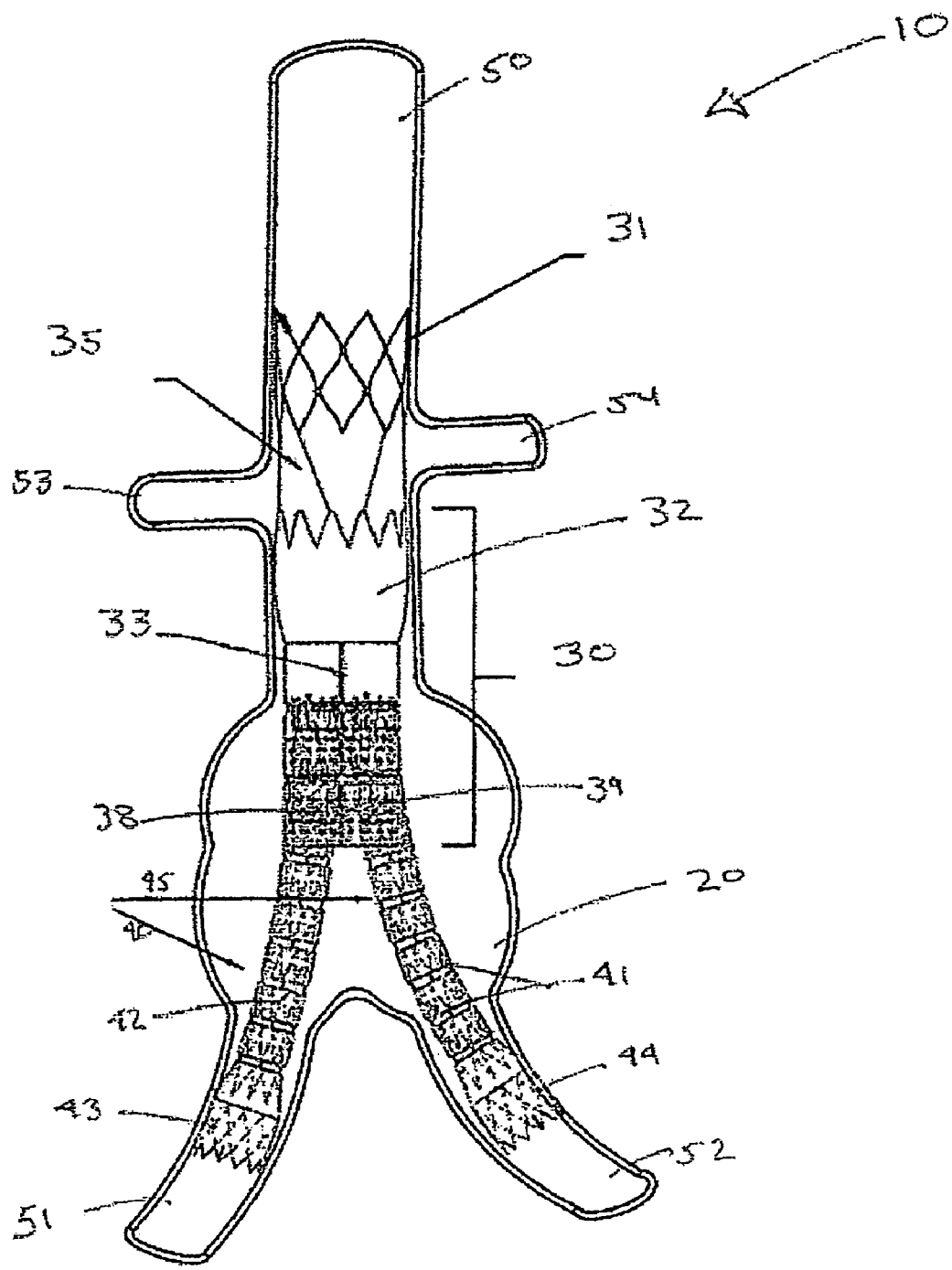
FIG. 1 illustrates an embodiment of a percutaneous endoprosthesis device with suprarenal fixation assembled in-situ to treat an abdominal aortic aneurysm according to the invention.

The various figures depict varying aspects of preferred embodiments of a suprarenal affixed endoprosthesis according to the invention. An endoprosthesis system configured according to the invention may be useful in assuring profiles more compatible with percutaneous delivery systems, assuring non-obstruction of the renal arteries, assuring non-traumatic holding of endolegs, achieving superior anchoring, and perhaps allowing for recapturability. As depicted in FIG. 1, the assembled endoprosthesis 10 may be configured to treat an abdominal aortic aneurysm 20. The prosthesis 10 includes a bifurcated trunk portion 30 and a pair of endolegs 40, 45 that provides a passageway for blood from the aorta 50 to safely flow into the iliac arteries 51, 52.

Figure 2:
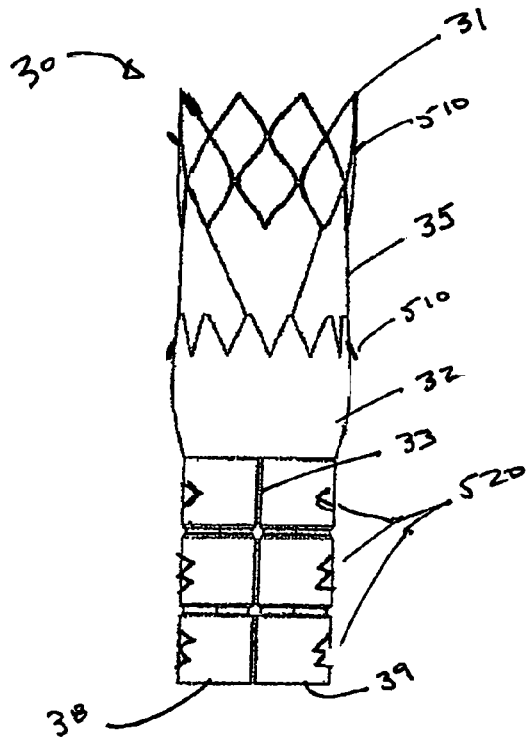
FIG. 2 is an isolation view of an embodiment of a bifurcated trunk portion of an unassembled endoprosthesis device according to the invention.

As shown in FIG. 2, the bifurcated trunk portion 30 comprises a suprarenal stent 31 attached to an aortal neck area 32 of a bifurcated body 33 via hanging sutures 35. When deployed, as depicted in FIG. 1, this configuration of the bifurcated trunk portion 30 allows for device fixation above the renal arteries via suprarenal stent 31. The hanging sutures 35 are sized so as to allow substantially unfettered flow of blood into the renal arteries 53, 54. Aortic proximal neck sealing is achieved in the aortal neck area 32 of the bifurcated body 33 in an area below the renal arteries 53, 54. The separation of the aortic proximal neck sealing of the device from the device fixation allows for the profile of the device to be reduced to sizes that make it compatible with true percutaneous delivery systems.

The suprarenal stent 31 may comprise any suitable stent or framework that provides for fixation in the aorta. In a preferred embodiment, the stent 31 comprises a nitinol stent, or other shape-memory alloy stent, that friction fits the stent in place via the nitinol expansion phenomena well known in the art.

The bifurcated body 33 is hung from the stent 31 via, e.g., sutures 35 in any suitable manner. Configuring sutures and achieving a suitable attachment and orientation of the bifurcated body 33 and the suprarenal fixation stent 31 are within the skill of those in the art.

The bifurcated body 33 preferably comprises a nitinol fabric having dimensions of a few microns or less. The nitinol fabric may be welded to a thin frame for sturdiness. In a preferred embodiment, the bifurcated body 33 comprises nitinol fabric with a non-kink reinforcement frame (not shown). The frame is preferably a thin nitinol stent that prevents kinking of the assembly. Moreover, preferably, when deployed, the trunk self-expands and seals the proximal aortic neck area of the abdominal aortic aneurysm.

In completing the assembly, the bifurcated trunk 30 is mated with the endolegs 40, 45 in situ. The endolegs of this embodiment comprise a pair of iliac leg endografts (ipsilateral and contralateral). The iliac leg endografts 40, 45 may be delivered and mated with the bifurcated trunk 30 via any suitable means. To achieve this end, the bifurcated trunk 30 includes an ipsilateral receiving tube 38 and a contralateral receiving tube 39, each configured to receive and be coupled to a respective iliac leg 40, 45.

Figure 3:
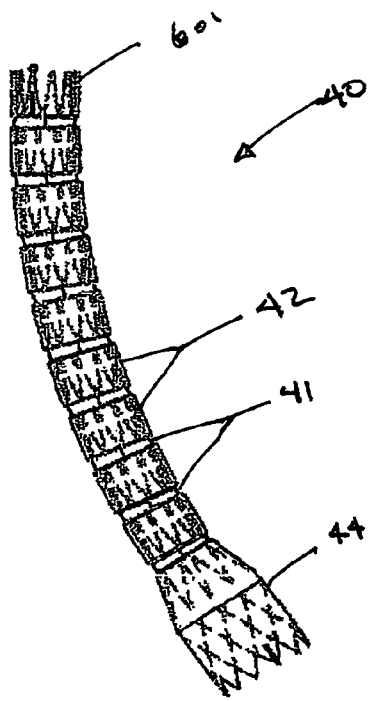
FIG. 3 is an isolation view of an embodiment of an iliac leg member of an unassembled endoprosthesis device according to the invention.

Any suitable configuration for the iliac legs 40, 45 are within the scope of the invention. In a preferred embodiment, the iliac legs 40, 45 comprise a sutured stent 41 to a polymeric graft 42. Preferably, as best shown in FIG. 3, the iliac legs 40, 45 comprise a polyester woven graft 42 onto which nitinol stent rings 41 are attached. Moreover, the distal end 43, 44 of the legs may be flared in a "bell bottom" configuration to enhance sealing and/or fixation to the iliac vessel 51, 52. Alternatively, the graft may also be made of a thermoplastic (i.e. polyester) material constructed as a knit, twill or other textile construction. Alternatively, the graft may be made of another suitable material. Regardless of the graft material used, the stent rings may be attached to the graft via sutures, adhesives, heat, or any other suitable means.

Figure 4:
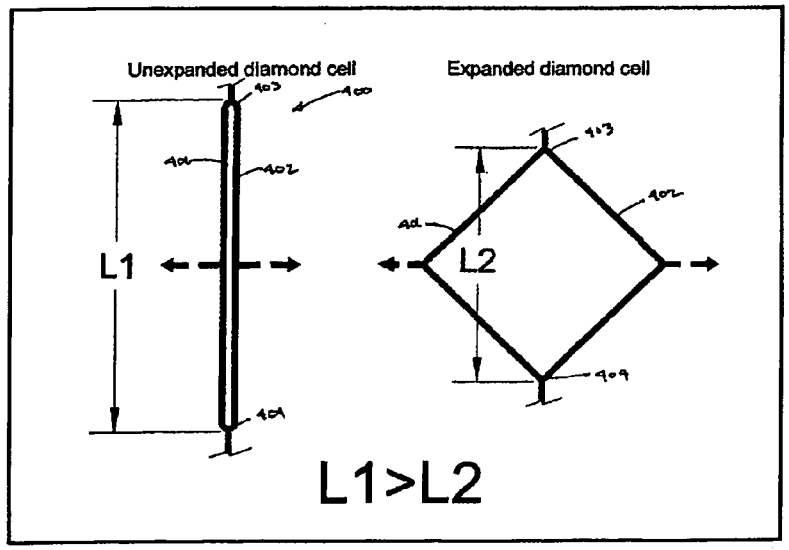
FIG. 4 illustrates the principle of foreshortening using a collapsed diamond shaped cell.

As will be appreciated, sealing and anchoring the various components of the devices may be desirable. This includes anchoring the stent ring 31 to the aortic wall, sealing the aortic proximal area of the bifurcated body with the aortic wall, anchoring and/or sealing the iliac legs with bifurcated body, sealing the iliac legs with the iliac vessels, and the like. The present invention provides novel anchoring and retaining mechanisms to achieve this end. As depicted in FIG. 4, the anchoring and retaining mechanisms of the present invention are based, in part, on the geometrical principle of differential foreshortening. As will be appreciated, when a straight line having a length (L1) between a first end and a second end is bent at a forty-five degree angle, the length or distance between the two ends shortens (L2). This principle is illustrated in FIG. 4. As shown, a collapsed diamond element 400 having sides 401, 402 of a given length (L1) spanning from a top end 403 and a bottom end 404 may be allowed to expand (get longer in the circumferential direction) into a diamond shape 401. The geometric result of such expansion, assuming the overall length of the sides remains constant, is that the second length (L2) between the top end 403 and bottom end 404, or the "height" of the diamond, is shorter than the original first length (L1), or "height" of the compressed structure.

FIG. 5 illustrates how the principle of differential foreshortening may be harnessed to achieve the advantageous anchoring and retention features according to the invention by the provision of an interior strut. By using a shape-memory alloy, or other collapsible framework, such as nitinol, a cell structure may be configured to allow for compression and expansion. In the depicted embodiment, a collapsible cell, such as diamond 500, includes opposing sides 501, 502 (which span a distance between a first end 503 and a second end 504) and a center strut 505. The placement of a strut 505 along the centerline of the cell, as exemplified in FIG. 5, is that as the height, or distance between the first end 503 and second end 504 is forced to shorten, so must the height of strut. This forced shortening can be harnessed during the nitinol expansion process. To be more particular, as the cell 500 expands to its diamond shape, the center strut 505 must bend out of plane to accommodate the shorter distance between the two ends 503, 504. This bending results in a projection out of plane with the two arms 501, 502. The height of the projection will be equal to the reduction in distance between the ends. For example, if the collapsed structure has arms 20 mm long, and if the structure expands into a perfect diamond (90° angles), then each side of the diamond will be 10 mm long and so will be the distance between the two ends. Accordingly, the center strut will have to bend 10 mm during expansion. This 10 mm bend can be configured to form a protrusion extending perpendicular from the sides. The geometry of the protrusion is a matter of design choice and will affect the height of the protrusion.

The cell is sized so that its expanded wingspan is a desired length and orientation suitable for the intended use of the cell. The cell is preferably one of a network of cells or included as part of a lattice of shape-memory material configured into a stent, endograft, or other intra-luminal device. The cell, and the overall device, may then be collapsed to a profile suitable for sheathing and delivery in catheterization procedures. The inclusion of a collapsible cell 500, or plurality of such cells, in a device such as the iliac leg receiving tubes 38, 39 of the bifurcated section 30 of the endoprosthesis of FIGS. 1-3 allows the forced shortening to be used to provide endoleg retention projections 510 to form in the inner diameter (ID) of device. As will be appreciated by one of ordinary skill in the art, use of these retention projections 510 provides for a method of non-traumatic holding of endolegs.

FIGS. 6A-B depict side views of various expanded cells to demonstrate the ability to configure the cell to result in retention projections 510 of various sizes and shapes. Creating thickened or thinned areas of the strut 505 will facilitate the bending of the strut to from desired geometries. A presently preferred embodiment is shown in FIG. 6B wherein a "W" shape is formed. The "W" shape of the retention projection 510 of the cell 500 may provide optimal alignment with the "windows" 601 of the iliac leg stents. FIG. 7 illustrates how the center strut 505 may be altered to result in alternately shaped retention projections 510. In FIG. 7, the strut 505 is configured into a "Y" shape. Upon bending, the mouth of the "Y" will result in a frame of a three-sided pyramid shape. One of ordinary skill in the art armed with the present specification will appreciated that the cells of the present invention may be modified in size, shape, orientation, and configuration to result in expanded structures having desired dimensions and features.

In this regard, FIG. 8 illustrates how the cell structure of FIG. 7 may be altered to include anchors. The cell 500 may be crafted to include flaring barbs 520. Preferably, barbs 520 will be sized and positioned to facilitate anchoring the stent, graft, endograft or overall device to the vessel in which it is being deployed. Accordingly, to achieve this type of anchoring, the barbs 520 are formed or deployed on the cell in a manner that allows for them to extend outside the outer diameter of the device. The use of barbs to anchor devices in vessels in known in the art and it is within the skill of the ordinary artisan to devise a construction that includes barbs of desired properties for the desired use. The anchors may be included with cells configured to provide retention projections upon expansion, or alternatively, be used to the exclusion of retention projections.

FIG. 9 depicts the use of a barb 520 and a strut 505 configuration that allows the barb to reside inside the cell frame when collapsed. Housing the barb in an interior area may reduce inadvertent pricks or snags while sheathing and deploying. FIG. 10 depicts a similar interior positioning of the barb 520, this time in a central location and wherein the barb 520 is adapted for deployment with a "W" shaped retention projection 510. FIG. 10 illustrates the potential for inclusion of multiple barbs 520 on a single cell member 500. In this embodiment, the cell 501 is configured to internally house the barbs 520 in its unexpanded state and flare the barbs outwardly from two sides of the retention mechanism during nitinol expansion. As will be appreciated, the geometry and configuration of the cells with projections and/or barbs is virtually limitless. Preferably, regardless of the configuration, only the barbs are designed to extend beyond the outer diameter of the device. This construction hinders the possibility of out-of-plane bending that could hamper the effectiveness of the anchoring. The use of the self-flaring barbs described herein helps reduce problems associated with sheathing devices having an anchor (hooks or barbs), and potentially allows for recapturability. Recapture may be achieved by reversing the differential shortening by causing the cell to collapse causing the barb to be retrieved into the interior of the cell.

The applicability of the retention projections and anchors described above to an endoprosthesis device such as those described herein is clear. Moreover, the use of the disclosed retention projections or anchors lends to crafting suitable alternate configurations of the device. For example, in an alternative embodiment to that depicted in FIG. 1, the bifurcated trunk may comprise a polymeric material and use a proximal neck stent placed in-situ for sealing of the bifurcated body to the proximal neck. Preferably, the neck stent includes self-flaring barbs for anchoring the device to the aortic wall. Also, the bifurcated trunk preferably includes cells having self-flaring endoleg retention projections for receiving and holding the iliac legs. Holding could be accomplished by hooking or mating with the proximal windows of the iliac legs or the stent gaps. In addition to these alternate embodiments, those skilled in the art will appreciate that various other adaptations and modifications of the above-described preferred embodiments and methods can be configured without departing from the scope and spirit of the invention. Therefore, it is to be understood that, within the scope of the appended claims, the invention may be practiced other than as specifically described herein.

We claim:

1. A percutaneous endoprosthesis device for treating an abdominal aortic aneurysm comprising:
   a bifurcated trunk and a pair of endolegs mateable with the trunk to serve as a conduit for blood flow to a patient's iliac arteries;
   the bifurcated trunk comprising a superenal stent structure connected to a bifurcated body portion via a plurality of sutures;
   the superenal stent structure being collapsible into a low profile configuration for percutaneous delivery and expandable into a deployed configuration wherein the superenal stent structure frictionally anchors to an interior of a vessel being treated;
   the bifurcated body portion having an aortic neck on a first end and a bifurcated leg section on a second end, the aortic neck having an outer wall comprising a nitinol fabric attached to a stent structure configured to seal with an interior wall of the vessel and the bifurcated leg section having an inner wall defining a pair of endoleg receiving tubes;
   the pair of endolegs configured for insertion into a respective endoleg tube of the bifurcated leg section of the bifurcated body portion of the bifurcated trunk;
   wherein the inner wall defining the endoleg receiving tubes each include multiple diamond shaped stent cells having at least one interiorly disposed endoleg retention projection, said retention projection in the form of a central strut connected apex to apex within the cell, the central strut being configured to deform out of the plane of the cell in a non-traumatic bend when the cell is expanded due to diamond foreshortening, the bend being configured to extend inwardly towards an endoleg and away from the artery.

* * * * *